United States Patent
Watanabe et al.

(10) Patent No.: US 8,568,301 B2
(45) Date of Patent: Oct. 29, 2013

(54) CONNECTOR SYSTEM

(75) Inventors: Masaaki Watanabe, Hachioji (JP); Koji Omori, Hachioji (JP); Masato Toda, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/567,370

(22) Filed: Aug. 6, 2012

(65) Prior Publication Data

US 2013/0035550 A1 Feb. 7, 2013

Related U.S. Application Data

(63) Continuation of application No. PCT/JP2011/055456, filed on Mar. 9, 2011.

(30) Foreign Application Priority Data

Mar. 16, 2010 (JP) ................................. 2010-059744

(51) Int. Cl.
  *A61B 1/00* (2006.01)
  *H01R 4/50* (2006.01)
(52) U.S. Cl.
  CPC ......... *A61B 1/00121* (2013.01); *A61B 1/00124* (2013.01)
  USPC .............................. 600/132; 439/348; 439/180
(58) Field of Classification Search
  USPC .......... 600/132, 134; 439/180, 259, 263, 298, 439/296, 348, 372, 638
  See application file for complete search history.

(56) References Cited

U.S. PATENT DOCUMENTS

| 4,404,964 | A | * | 9/1983 | Kambara | 600/163 |
| 4,414,608 | A | * | 11/1983 | Furihata | 362/574 |
| 4,919,627 | A | * | 4/1990 | Cable | 439/263 |
| 5,702,345 | A | * | 12/1997 | Wood et al. | 600/109 |
| 5,984,709 | A | * | 11/1999 | Zink et al. | 439/348 |
| 7,331,813 | B2 | * | 2/2008 | Tsujita | 439/348 |
| 7,749,003 | B2 | * | 7/2010 | Omori | 439/137 |
| 7,959,471 | B2 | * | 6/2011 | Omori | 439/630 |
| 2007/0254514 | A1 | * | 11/2007 | Weksler et al. | 439/296 |
| 2008/0269560 | A1 | * | 10/2008 | Ito et al. | 600/132 |

(Continued)

FOREIGN PATENT DOCUMENTS

| EP | 2 096 716 A2 | 9/2009 |
| GB | 2 320 622 A | 6/1998 |

(Continued)

OTHER PUBLICATIONS

European Search Report Jul. 11, 2013 from corresponding European Application No. 11 75 6146.4.

*Primary Examiner* — John P Leubecker
(74) *Attorney, Agent, or Firm* — Scully, Scott, Murphy & Presser, P.C.

(57) ABSTRACT

A connector system includes a plug section, and a receptacle section having a concave portion in an inside of which the plug section can be inserted, wherein the plug section includes a flange portion including a first inclined surface portion which increases in diameter toward an extraction direction, and a second inclined surface portion which decreases in diameter toward the extraction direction on an extraction direction side of the first inclined surface portion, in which an inclination angle with respect to an insertion direction of the second inclined surface portion is larger than an inclination angle with respect to the insertion direction of the first inclined surface portion, and the receptacle section includes a ball which is placed to be projectable/retractable from a side surface portion of the concave portion.

1 Claim, 11 Drawing Sheets

(56) References Cited

U.S. PATENT DOCUMENTS

2008/0281157 A1* 11/2008 Miyagi et al. ............ 600/132
2009/0215311 A1* 8/2009 Omori ...................... 439/577

FOREIGN PATENT DOCUMENTS

| JP | 05-300874 | 11/1993 |
| JP | 08-321350 A | 12/1996 |
| JP | 09-329285 A | 12/1997 |
| JP | 10-295635 | 11/1998 |
| JP | 2000-65277 A | 3/2000 |
| JP | 2000-283366 A | 10/2000 |
| JP | 2001-4085 A | 1/2001 |
| JP | 2002-034912 | 2/2002 |
| JP | 2008-220463 A | 9/2008 |
| JP | 2009-273652 | 11/2009 |

* cited by examiner

EXTRACTION DIRECTION
INSERTION DIRECTION

CONNECTOR SYSTEM

CROSS REFERENCE TO RELATED APPLICATION

This application is a continuation application of PCT/JP2011/055456 filed on Mar. 9, 2011 and claims benefit of Japanese Application No. 2010-059744 filed in Japan on Mar. 16, 2010, the entire contents of which are incorporated herein by this reference.

BACKGROUND OF THE INVENTION

1. Field of the Invention

The present invention relates to a connector system that connects electric contact points provided at both a plug section and a receptacle section.

2. Description of the Related Art

An endoscope which is used in a medical field is generally used in a state in which the endoscope is connected to outside equipment such as a light source apparatus which emits an illuminating light, and an image processing apparatus for displaying an image picked up by driving an image pickup apparatus. Japanese Patent Application Laid-Open Publication No. 2002-34912 discloses an endoscope apparatus including a connector system in which two kinds of connectors are integrated, which are a connector that connects light guide fibers which are inserted through an endoscope and a light source apparatus, and a connector which electrically connects an image pickup section placed in the endoscope and an image processing apparatus, in order to facilitate a connecting operation of the endoscope, and the light source apparatus and the image processing apparatus.

SUMMARY OF THE INVENTION

A connector system according to an aspect of the present invention is a connector system including a plug section provided at a universal cord section of an endoscope, a land provided at the plug section and having conductivity, a receptacle section provided at a control section to which the endoscope is connected to receive a signal from the endoscope via the land, and having a concave portion in an inside of which the plug section can be inserted, and a contact point provided at the receptacle section and having conductivity, in which the plug section is inserted into or extracted from the receptacle section, whereby the land and the contact point are caused to abut on each other or separate from each other, wherein the plug section includes a flange portion including a first inclined surface portion which increases in diameter toward an extraction direction, and a second inclined surface portion which decreases in diameter toward the extraction direction on an extraction direction side of the first inclined surface portion, in which an inclination angle with respect to an insertion direction of the second inclined surface portion is larger than an inclination angle with respect to the insertion direction of the first inclined surface portion, and the receptacle section includes a ball which is placed to be projectable/retractable from a side surface portion of the concave portion, and to be capable of abutting on the first inclined surface portion and the second inclined surface portion of the flange portion when the plug section is inserted, and an urging member which urges the ball in a direction to project into the concave portion from the side surface portion.

DETAILED DESCRIPTION OF THE PREFERRED EMBODIMENT

Figure 1:
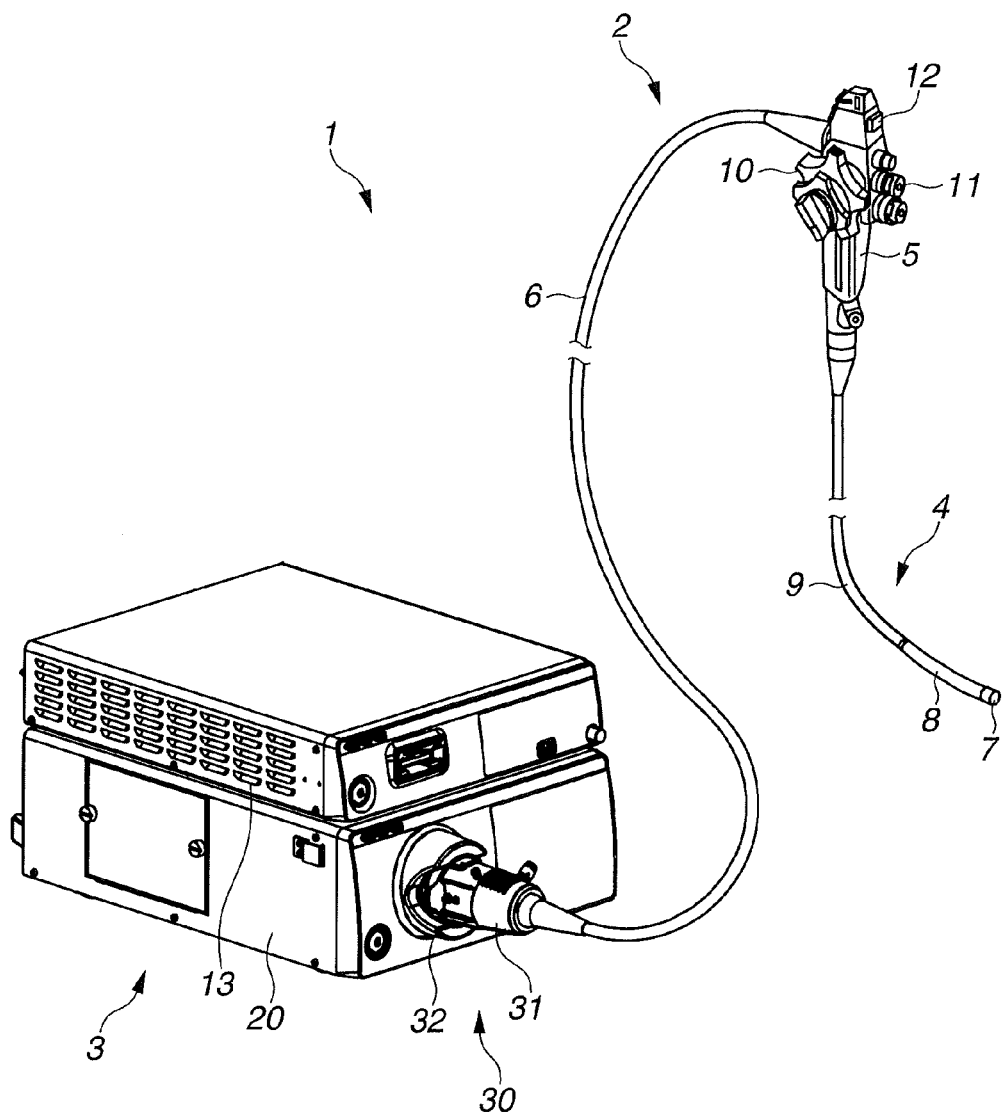
FIG. 1 is a view showing an entire configuration of an endoscope apparatus.

Hereinafter, a preferred embodiment of the present invention will be described with reference to the drawings. It should be noted that in each of the drawings for use in the following description, the scale is made to differ at each component in order to make each component to be in such a size as to be recognizable on the drawing, and the present invention is not limited to the numbers and the amounts of the components, the shapes of the components, the ratios of the sizes of the components, and the relative positional relationships of the respective components, which are described in the drawings.

Hereinafter, an example of application of a connector system according to the present invention to an endoscope apparatus 1 shown in FIG. 1 will be described. The endoscope apparatus 1 is configured by including an endoscope 2 and a control section 3 as shown in FIG. 1. The endoscope apparatus 1 includes a connector system 30 according to the present invention, and the endoscope 2 and the control section 3 are detachably connected via the connector system 30.

The endoscope apparatus 1 of the present embodiment has a configuration which optically picks up an image of a predetermined observation site in an object to be examined such as a human body, and outputs the image to a display apparatus not illustrated, as one example. The endoscope apparatus 1 may be in the mode which is referred to as a so-called ultrasound endoscope which picks up an ultrasound tomographic image of a predetermined observation site of an object to be examined.

The endoscope 2 is configured by mainly including an insertion portion 4 which can be introduced into a body of an object to be examined, an operation section 5 which is located at a proximal end of the insertion portion 4, and a universal cord 6 which is extended from a side portion of the operation section 5.

The insertion portion 4 is configured by a distal end portion 7 placed at a distal end, a bendable bending portion 8 which is placed at a proximal end side of the distal end portion 7, and a flexible tube portion 9 which is placed at a proximal end side of the bending portion 8, is connected to a distal end side of the operation section 5 and has flexibility, being connectively provided. The endoscope 2 may be of a mode referred to as a so-called rigid endoscope which does not include a site having flexibility in the insertion portion 4.

The distal end portion 7 of the insertion portion 4 is provided with an image pickup section and an illumination section for picking up an optical image, and an opening. The image pickup section is configured by including an image pickup apparatus including an image pickup device which is generally referred to as a CCD or a CMOS sensor and an electric circuit which drives the image pickup device, and an image pickup lens for forming an object image on a light receiving surface of the image pickup device. The image pickup apparatus is electrically connected to an image processing apparatus 13 which is provided at the control section 3 which will be described later via an electric cable which is inserted through the endoscope 2.

More specifically, in the present embodiment, the image pickup apparatus is operated by electric power and a drive signal which are inputted via the electric cable from the control section 3, and outputs a video signal to the control section 3 via an electric cable. Further, the image pickup lens has a so-called electrically-operated zoom mechanism with a shooting magnifying power changeable by an electrically-operated actuator such as a stepping motor. A control signal and electric power for driving the electrically-operated zoom mechanism are inputted via the electric cable from the control section.

Further, the illumination section is connected to a light source apparatus 20 provided at the control section 3 which will be described later via an optical fiber cable which is inserted through the endoscope 2, and is for emitting a light emitted from the light source apparatus 20 toward an object of the image pickup section. Configurations of the image pickup section and the illumination section in the endoscope 2 are well known, and therefore, the detailed description thereof will be omitted.

Further, one or a plurality of openings are provided at the distal end portion 7. At least one of the openings provided at the distal end portion 7 communicates with an air supply apparatus section 22 provided in the control section 3 which will be described later via a conduit which is inserted through the endoscope 2, and is for performing delivery of at least one fluid of air and a liquid. A coil which is used in an endoscope shape detecting apparatus which detects a position of the distal end portion 7 and a shape of the insertion portion 4 may be placed in the insertion portion 4 of the endoscope 2.

The operation section 5 is provided with an angle knob 10 for operating bending of the bending portion 8, an air supply/water supply button 11 for performing control of a delivery operation of the fluid from the opening provided at the distal end portion 7, and a button switch 12 for inputting operation instructions of a zoom operation, still image shooting and the like of the image pickup section. The button switch 12 is electrically connected to the control section 3 which will be described later, via an electric cable which is inserted through the universal cord 6.

A plug section 31 configuring the connector system 30 is provided at a proximal end portion of the universal cord 6.

Though the details will be described later, the plug section 31 has a configuration that can be inserted into a receptacle section 32 in a substantially concave shape which is provided at the control section 3 and configures the connector system 30. In the endoscope apparatus 1 of the present embodiment, connection and separation to and from the electric circuit, the optical fiber cable and the conduit which are placed in the endoscope 2, and the control section 3 are performed by the connector system 30.

Figure 2:
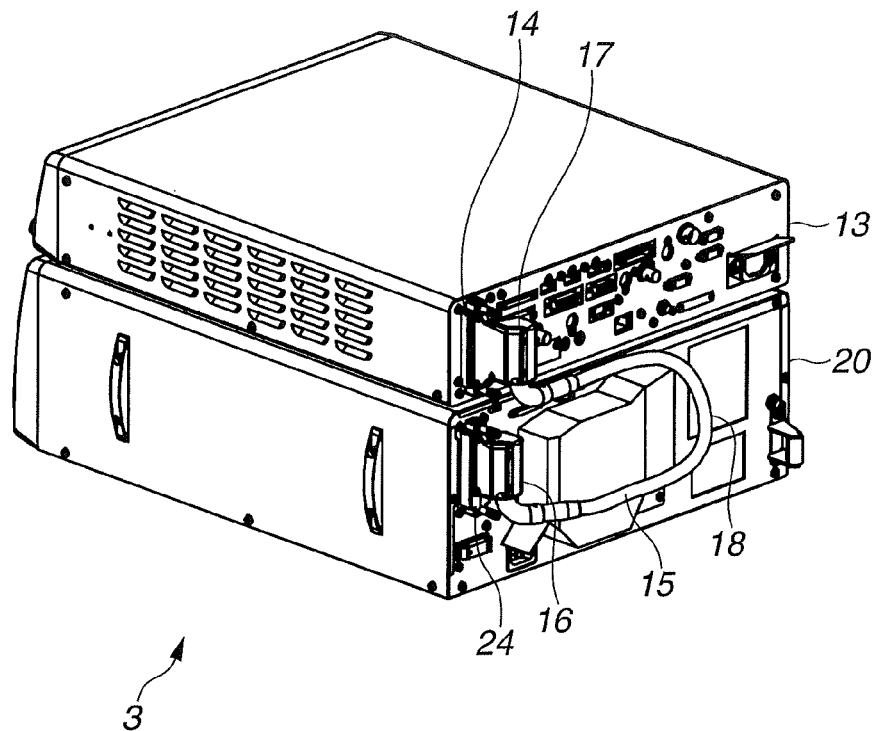
FIG. 2 is a perspective view of a control section seen from a rear side.

The control section 3 is configured by including the image processing apparatus 13 and the light source apparatus 20 as shown in FIG. 1 and FIG. 2. In the present embodiment, the image processing apparatus 13 and the light source apparatus 20 are respectively housed in casings in substantially rectangular parallelepiped shapes which are separated. In the following description, a surface which is one of four surfaces, except for the surfaces facing an upper side and a lower side out of surfaces configuring each of the casings of the image processing apparatus 13 and the light source apparatus 20 in the substantially rectangular parallelepiped shapes, and faces a user at the time of use of the endoscope apparatus 1 will be referred to as a front surface. Further, a surface at an opposite side of the front surface will be referred to as a rear surface.

At the time of use of the endoscope apparatus 1 of the present embodiment, the image processing apparatus 13 is placed on a top surface of the light source apparatus 20, as shown in FIG. 1. As shown in FIG. 2, the light source apparatus 20 and the image processing apparatus 13 are electrically connected via a connection cable 15 which is an electric cable.

More specifically, on the rear surfaces of the light source apparatus 20 and the image processing apparatus 13, a light source apparatus side receptacle 24 and an image processing apparatus side receptacle 14 are respectively provided. Further, the connection cable 15 is configured by having a light source apparatus side plug 16 detachable from the light source apparatus side receptacle 24 at one end, and an image processing apparatus side plug 17 detachable from the image processing apparatus side receptacle 14 at the other end.

More specifically, the combination of the light source apparatus side receptacle 24 and the light source apparatus side plug 16, and the combination of the image processing apparatus side receptacle 14 and the image processing apparatus side plug 17 configure a pair of electric connectors including so-called female side connectors and male side connectors. In the endoscope apparatus 1 of the present embodiment, the pair of electric connectors has different fitting shapes respectively, and is configured so that connection with different combinations is impossible. In other words, in the present embodiment, it is impossible to connect the light source apparatus side plug 16 of the connection cable 15 to the image processing apparatus side receptacle 14, and it is impossible to connect the image processing apparatus side plug 17 of the connection cable 15 to the light source apparatus side receptacle 24.

As the configuration which makes a pair of electric connectors in the different fitting shapes respectively, for example, the configuration is conceivable, in which sites in the shapes to be so-called keys and key grooves are provided in the fitting portions, and the positions and the numbers of the keys and the key grooves are made different in accordance with the combinations. Further, for example, the configuration may be adopted, in which the fitting shape of one of the electric connectors is made substantially circular, and the fitting shape of the other connector is made substantially rectangular.

As above, the connection cable 15 which connects the light source apparatus 20 and the image processing apparatus 13 is prevented from being connected in the different orientation, whereby an operation error in a preparation operation for use of the endoscope apparatus 1 can be prevented, and a quick and reliable preparation operation for use can be enabled. Further, when keys and key grooves are provided at the fitting portions of the electric connectors, the male connectors cannot be inserted from the erroneous direction to the female connectors, and therefore, connection of the electric connectors in a state in which conduction is unreliable, which is referred to as so-called oblique insertion can be prevented, which is more preferable.

The connection cable 15 of the present embodiment extends to be along the rear surfaces of the light source apparatus 20 and the image processing apparatus 13 in the state in which the connection cable 15 connects the light source apparatus 20 and the image processing apparatus 13 as shown in FIG. 2. More specifically, the insertion direction of the light source apparatus side plug 16 and the image processing apparatus side plug 17 to the light source apparatus side receptacle 24 and the image processing apparatus side receptacle 14 and the extending direction of the connection cable 15 are substantially orthogonal to each other. The connection cable 15 has such a length as to allow a substantially U-shaped folded portion 18 to be provided, in the state in which the connection cable 15 connects the light source apparatus 20 and the image processing apparatus 13.

As above, the connection cable 15 is extended along the rear surfaces of the light source apparatus 20 and the image processing apparatus 13, and the folded portion 18 in the substantially U shape is provided at the connection cable 15, whereby when the control apparatus 3 is installed, a necessary space for the rear side of the control apparatus 3 can be made small.

Further, according to the present embodiment, load which is applied to the light source apparatus side receptacle 24, the light source apparatus side plug 16, the image processing apparatus side receptacle 14 and the image processing apparatus side plug 17 when a matter contacts the connection cable 15, and when the positions of the light source apparatus 20 and the image processing apparatus 13 are displaced from each other can be reduced.

The image processing apparatus 13 has a configuration which controls the operations of the image pickup apparatus and the image pickup lens which are placed in the endoscope 2, and has a configuration which performs conversion processing of a video signal outputted from the image pickup apparatus to make the video signal displayable on a display apparatus not illustrated, and outputs the video signal.

More specifically, the image processing apparatus 13 is configured by including a first control section which outputs electric power and a drive signal for driving the image pickup apparatus which includes the image pickup device, and performs conversion processing of a video signal outputted from the image pickup apparatus, and a second control section which outputs electric power and a drive signal for driving the electrically-operated zoom mechanism of the image pickup lens.

Figure 3:
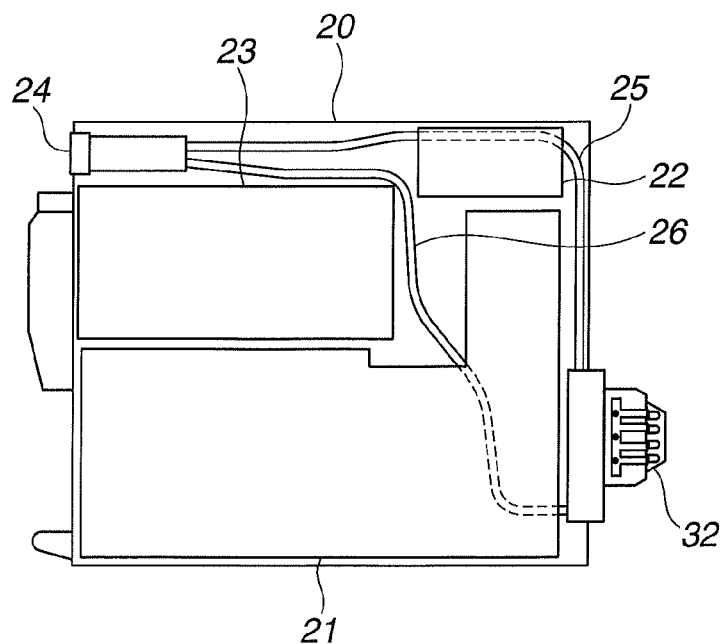
FIG. 3 is a view showing a schematic interior configuration of a light source apparatus 20.

The light source apparatus 20 is configured by including the receptacle section 32, a light source section 21, the air supply apparatus section 22 and a power supply section 23, as shown in FIG. 3.

The receptacle section 32 configures the connector system 30, and has a concave shape in an inside of which the plug section 31 provided at the endoscope 2 can be inserted, though the details will be described later. In the present embodiment, the receptacle section 32 is provided on the front surface of the light source apparatus 20.

The light source section 21 is placed at a rear side of the receptacle section 32. The light source section 21 has a light source which emits a light with a wavelength to which the image pickup section of the endoscope 2 has sensitivity, such as a halogen lamp, a xenon lamp, an LED or a semiconductor laser, for example. The light emitted from the light source section 21 is incident on the receptacle section 32.

Further, though not illustrated, the light source section 21 has an optical system member for causing the light emitted by the light source to be efficiently incident on the optical fiber cable which is inserted through the endoscope 2. The light source section 21 may be of a mode including a band path filter and a polarizing filter.

The air supply apparatus section 22 is configured by including an electrically-operated pump which discharges air for being delivered from the opening of the distal end portion 7 of the insertion portion 4 of the endoscope 2, in the present embodiment. The air supply apparatus section 22 is connected to the receptacle section 32 via a conduit not illustrated. The air supply apparatus section 22 can have a configuration which discharges air with a predetermined pressure, such as an electrically-operated pump, a compressor or a bomb, and may have the configuration which is provided at an exterior of the endoscope apparatus 1.

The power supply section 23 is an apparatus which supplies electric power for driving the light source section 21 and the air supply apparatus section 22.

Further, as described above, the light source apparatus side receptacle 24 is provided at the rear surface of the light source apparatus 20. The receptacle section 32 which is provided on the front surface, and the light source apparatus side receptacle 24 which is provided on the rear surface are electrically connected by a first harness 25 and a second harness 26 which are cabled in the casing of the light source apparatus 20.

The first harness 25 is configured by a plurality of electric cables which transmit electric power for driving the image pickup apparatus of the endoscope 2, a control signal which controls the operation of the image pickup apparatus, and a video signal outputted from the image pickup apparatus. In the light source apparatus 20, the first harness 25 is extended in the direction to be away with respect to the light source section 21 from the receptacle section 32 and is cabled to be apart from the light source section 21 by a predetermined distance or more.

The image pickup apparatus which is placed in the endoscope 2 and includes the image pickup device is electrically connected to the first control section of the image processing apparatus 13 via the first harness 25 and the connection cable 15. Hereinafter, an electric circuit including the image pickup apparatus and the first control section, and a plurality of electric cables which electrically connect both of the image pickup apparatus and the first control section will be referred to as a first electric circuit.

The second harness 26 is configured by a plurality of electric cables for transmitting a control signal and electric power for driving the electrically-operated zoom mechanism of the image pickup lens of the endoscope 2. Further, for example, when the endoscope apparatus 1 has the endoscope shape detecting apparatus, the second harness 26 includes an electric cable for supplying electric power to a coil which is placed in the insertion portion 4. The second harness 26 is cabled in a state in which the second harness 26 is apart from the first harness 25, between the first harness 25 and the light source section 21.

The electrically-operated zoom mechanism of the image pickup lens placed in the endoscope 2 is electrically connected to the second control section of the image processing apparatus 13 via the second harness 26 and the connection cable 15. Hereinafter, an electric circuit including the electrically-operated zoom mechanism and the second control section, and a plurality of electric cables which electrically connect both the electrically-operated zoom mechanism and the second control section will be referred to as a second electric circuit. When the endoscope apparatus 1 has the endoscope shape detecting apparatus, the coil which is placed in the insertion portion 4 and the electric cable for supplying electric power to the coil are also included in the second electric circuit.

In the present embodiment, the electric cables extended from the receptacle section 32 are distributed to a plurality of harnesses, whereby flexibility of the individual harnesses is enhanced, and the degree of freedom of routing is enhanced.

Further, in the present embodiment, in the light source apparatus 20, the first harness 25 which configures the first electric circuit, and the second harness 26 which configures the second electric circuit are apart from each other. By the configuration like this, the influence which the electromagnetic noise generated by the second electric circuit exerts on the fist electric circuit which drives the image pickup section at the time of operation of the electrically-operated zoom mechanism or the like can be suppressed.

Further, in the present embodiment, in the light source apparatus 20, the first harness 25 which configures the first electric circuit is cabled to be apart from the light source section 21 by the predetermined distance or more, and therefore, the influence exerted by the electromagnetic noise which is generated from the light source section 21 that is an electromagnetic noise source on the first electric circuit which drives the image pickup section can be suppressed.

Hereinafter, a configuration of the connector system 30 of the present embodiment will be described. As described above, the connector system 30 is configured by the plug section 31 provided at the proximal end portion of the universal cord 6 of the endoscope 2, and the receptacle section 32 provided at the control section 3. The present embodiment has the configuration in which the plug section 31 which is a so-called male side connector in a substantially convex shape is inserted into the receptacle section 32 which is a so-called female side connecter in a substantially concave shape, whereby the electric circuits, the optical fiber cables, and the conduits which are placed in the endoscope 2 are collectively connected to the control section 3.

Figure 4:
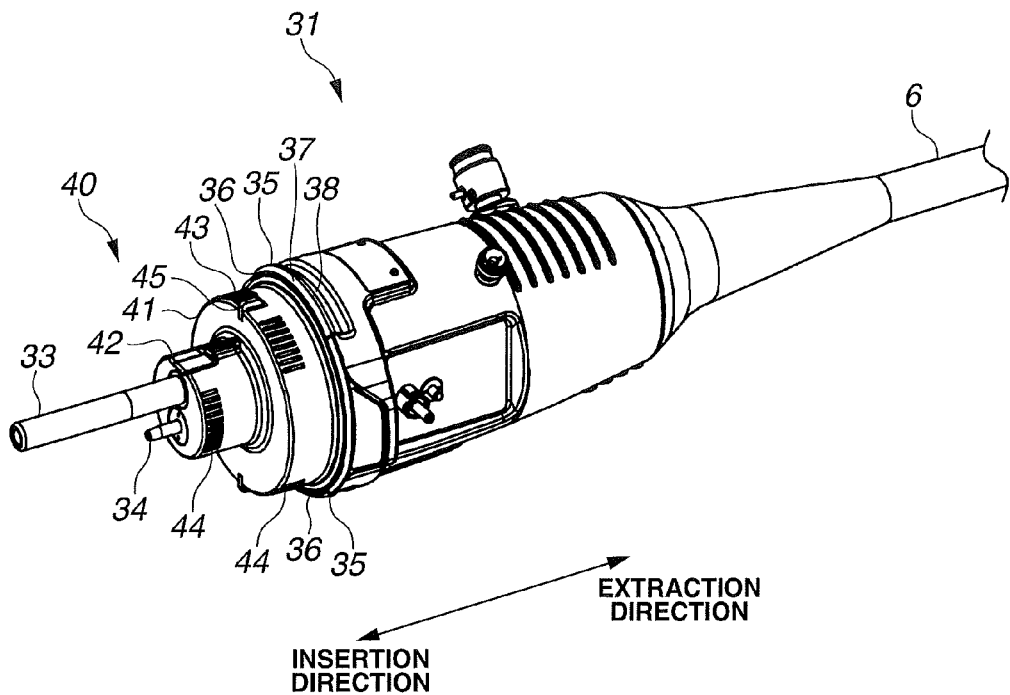
FIG. 4 is a perspective view of a plug section.
Figure 5:
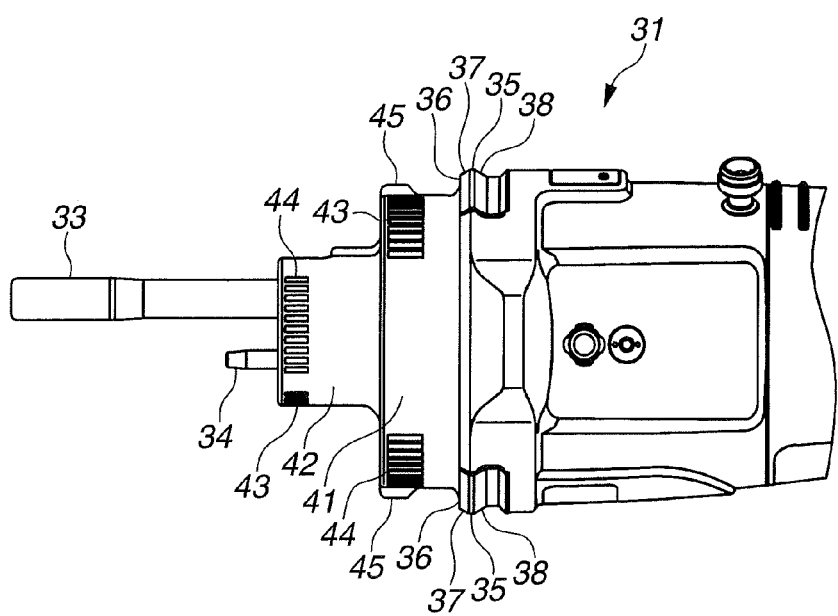
FIG. 5 is a side view of the plug section.

First, a configuration of the plug section 31 will be described. As shown in FIG. 4 and FIG. 5, the plug section 31 is configured by including an electric connector portion 40, a light guide plug 33, a conduit plug 34 and a flange portion 35. In the following description, a direction in which the plug section 31 is inserted into the receptacle section 32 will be referred to as an insertion direction, and a direction opposite to the insertion direction, that is, the direction in which the plug section 31 is extracted from the receptacle section 32 will be referred to as an extraction direction.

The electric plug portion 40, the light guide plug 33, and the conduit plug 34 respectively have outer circumferential shapes in substantially circular shapes. Respective center axes of the electric plug portion 40, the light guide plug 33, and the conduit plug 34 are substantially parallel with one another, and the center axes are placed to be along the insertion direction.

The electric plug portion 40 has such an outside diameter that a first housing 41 and a second housing 42 in substantially circular column shapes with the axes along the insertion direction as center axes are connected in the insertion direction. The second housing 42 is provided at the insertion direction side of the first housing 41, and an outside diameter of the second housing 42 is smaller than an outside diameter of the first housing 41.

In the present embodiment, the first housing 41 and the second housing 42 may formed by integral molding of a synthetic resin material with electric insulation properties. The center axes of the first housing 41 and the second housing 42 can be substantially parallel with each other. In the present embodiment, the center axis of the second housing 42 is offset by a predetermined distance in the radial direction with respect to the center axis of the first housing 41.

On an outer circumferential portion of the first housing 41, a plurality of first electric circuit lands 43 and second electric circuit lands 44 which are lands having conductivity are provided. Further, also on an outer circumferential portion of the second housing 42, a plurality of first electric circuit lands 43 and second electric circuit lands 44 are provided.

The first electric circuit land 43 is electrically connected to the image pickup apparatus via the electric cable inserted through the endoscope 2. More specifically, the first electric circuit land 43 configures a part of the first electric circuit. The first electric circuit is an electric circuit including the image pickup apparatus, the first control section of the image processing apparatus 13 and a plurality of electric cables which electrically connect both the image pickup apparatus and the first control section, as described above.

Further, the second electric circuit land 44 is electrically connected to the electrically-operated zoom mechanism of the image pickup section via the electric cable inserted through the endoscope 2. More specifically, the second electric circuit land 44 configures a part of the second electric circuit. The second electric circuit is an electric circuit including the electrically-operated zoom mechanism, the second control section of the image processing apparatus 13, and a plurality of electric cables which electrically connect the electrically-operated zoom mechanism and the second control section as described above.

In the respective outer circumferential portions of the first housing 41 and the second housing 42, the first electric circuit lands 43 and the second electric circuit lands 44 are placed in two regions which are apart in a circumferential direction with the center axis therebetween. The first electric circuit lands 43 and the second electric circuit lands 44 are made apart in the circumferential direction in this manner, whereby a creepage distance and a clearance distance between the different electric circuits can be taken to be large.

Further, a projection portion 45 which projects to outside in the radial direction is provided at the outer circumferential portion of the first housing 41. The projection portion 45 plays a role of a so-called key in the fitting mechanism, and is provided at a position corresponding to a groove portion 57 which is a key groove provided at the receptacle section 32 which will be described later. One projection portion 45 or a plurality of projection portions 45 may be provided.

At the end surface portion at the insertion direction side of the electric plug section 40 as above, the light guide plug 33 and the conduit plug 34 are projectingly provided. More specifically, the light guide plug 33 and the conduit plug 34 are provided to extend in the insertion direction from the end surface portion at the insertion direction side of the second housing portion 42.

The light guide plug 33 is a member in a substantially cylindrical shape, which houses terminal end portions (proximal end portions) of the light guide fibers which are inserted through the endoscope 2. The light guide plug 33 is opened in the insertion direction, and the terminal ends of the light guide fibers are exposed in the insertion direction from the opening. Further, the conduit plug 34 is a member in a substantially cylindrical shape which communicates with the conduit which is inserted through the endoscope 2.

At the side opposite from the insertion direction of the electric plug section 40, that is, at the extraction direction side, the flange portion 35 is provided. The flange portion 35 has a shape which is projects to outside in the radial direction from the electric plug section 40.

In the present embodiment, the flange portion 35 has a circular outer circumferential shape with an outside diameter larger than the first housing 41, and is provided so that a center axis thereof substantially corresponds to the center axis of the first housing 41. The flange portion 35 may be in the mode provided at an entire periphery with respect to the circumferential direction, or may be in the mode provided at one part in the circumferential direction.

The flange portion 35 is made of a material having conductivity such as a metal like, for example, a stainless alloy, and is electrically connected to an electromagnetic shield member which is a conductive member with which a periphery of the electric circuit placed in the endoscope 2 is covered. The flange portion 35 itself may have a cylindrical shape of a metal with which an outer periphery of the plug section 31 is covered, and may be configured to work as an electromagnetic shield member.

Figure 6:
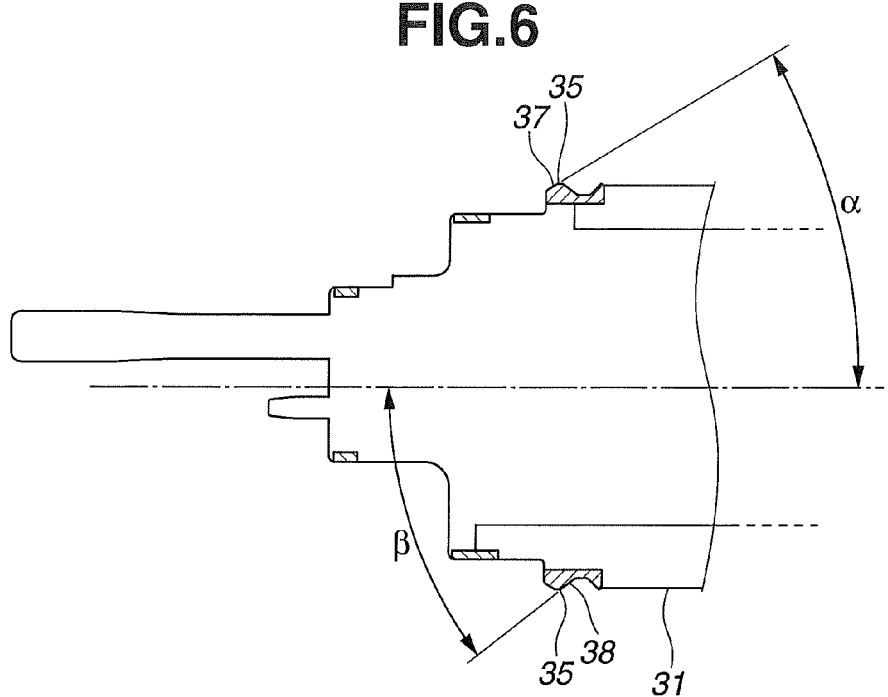
FIG. 6 is a view showing inclination angles of a first inclined surface portion and a second inclined surface portion of a flange portion.

The flange portion 35 is configured by three surfaces that are a butt surface portion 36, a first inclined surface portion 37 and a second inclined surface portion 38, as shown in FIG. 5 and FIG. 6. The butt surface portion 36 is a plane which faces in the insertion direction, and is orthogonal to the center axis. The butt surface portion 36 is a site for performing positioning in the insertion direction of the plug section 31 with respect to the receptacle section 32 by butting against a bottom surface portion 64 of a concave portion 63 which will be described later that is provided at the receptacle section 32 when the plug section 31 is inserted in the receptacle section 32.

The fist inclined surface portion 37 is a so-called tapered surface which increases in diameter to outside in a radial direction toward the extraction direction, on an extraction direction side of the butt surface portion 36. Here, an angle of inclination of the first inclined surface portion 37 with respect to the center axis (insertion direction) of the flange portion 35 is set as an inclined angle α.

The second inclined surface portion 38 is a so-called tapered surface which decreases in diameter to inside in the radial direction toward the extraction direction on an extraction direction side of the first inclined surface portion 37. Here, an angle of inclination of the second inclined surface portion 38 with respect to the center axis (insertion direction) of the flange portion 35 is set as an inclined angle β. In the present embodiment, the inclined angle β of the second inclined surface portion 38 of the flange portion 35 is set to be larger than the inclined angle α of the first inclined surface portion.

Figure 7:
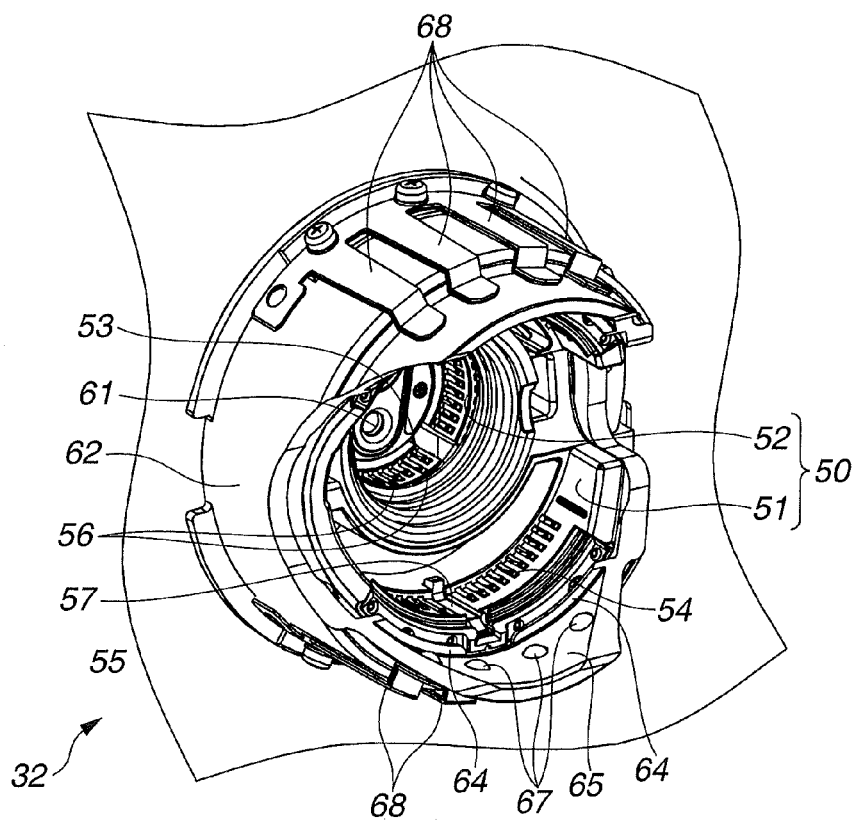
FIG. 7 is a perspective view of a receptacle section.
Figure 8:
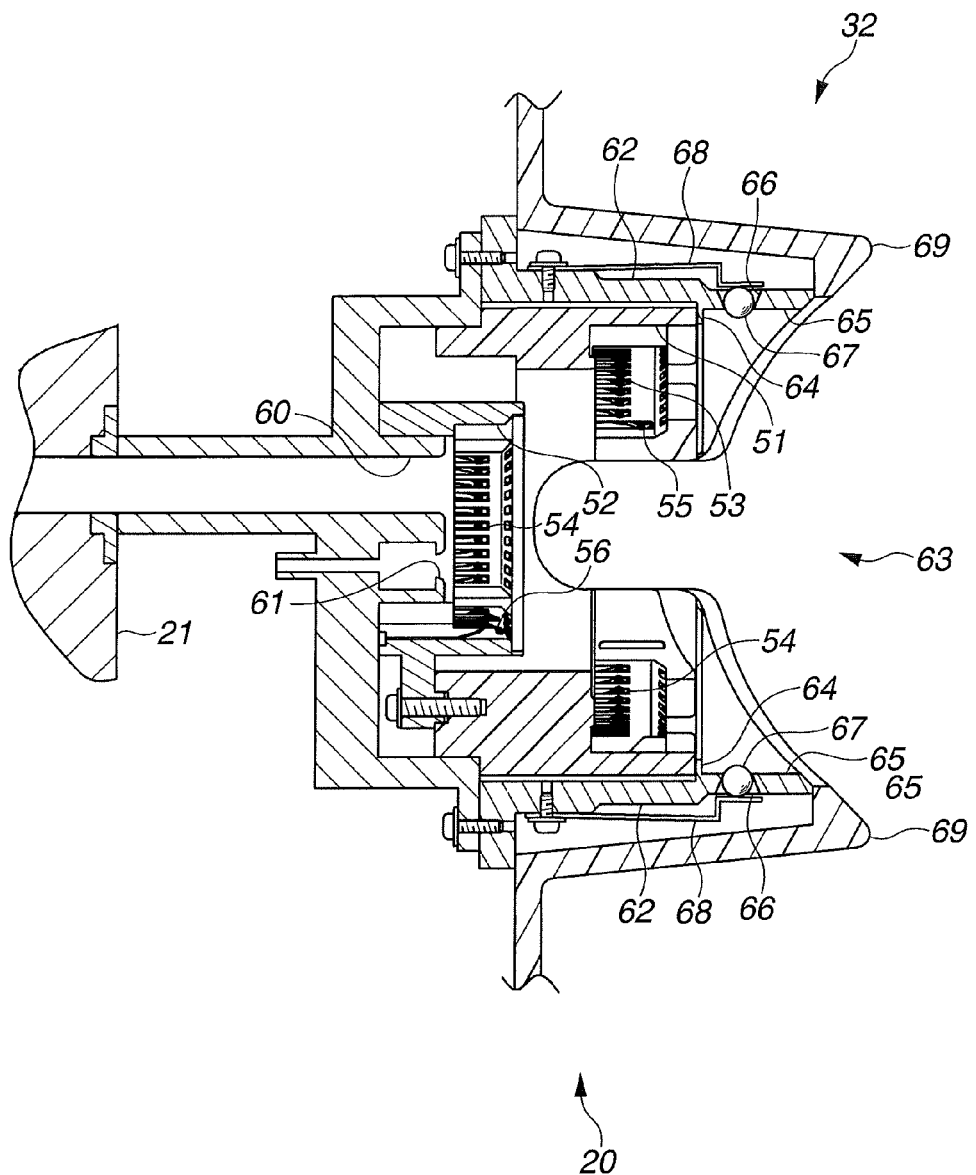
FIG. 8 is a sectional view showing a schematic configuration of the receptacle section.

Next, a configuration of the receptacle section 32 will be described. The receptacle section 32 has a substantially concave shape in an inside of which the plug section 31 can be inserted as shown in FIG. 7 and FIG. 8. The receptacle section 32 is configured by including an electric receptacle portion 50, a light guide receptacle portion 60 and a conduit receptacle portion 61.

The electric receptacle portion 50 is a substantially circular concave portion which houses the electric plug section 40 with a predetermined clearance. More specifically, the electric receptacle portion 50 is configured by including a first concave portion 51 having such an inside diameter as to house the first housing 41 with a predetermined clearance, and a second concave portion 52 which is provided at a bottom surface portion of the first concave portion 51 and has such an inside diameter as to house the second housing 42 with a predetermined clearance.

The first concave portion 51 and the second concave portion 52 are formed by a synthetic resin material with electrical insulation properties in the present embodiment. The first concave portion 51 and the second concave portion 52 are provided so that center axes are offset in accordance with the offset amount of the center axes of the first housing 41 and the second housing 42. By adoption of the configuration like this, the plug section 31 can be prevented from being inserted into the receptacle section 32 at an erroneous angle.

At inner surface portions of the first concave portion 51 and the second concave portion 52, a plurality of first electric circuit contact points 53 and second electric circuit contact points 54 which are contact points having conductivity are provided to project to inside in the radial direction. The first electric circuit contact point 53 and the second electric circuit contact point 54 are configured to abut on the first electric circuit land 43 and the second electric circuit land 44 in a state in which the plug section 31 is inserted into the receptacle section 32.

The first electric circuit contact point 53 and the second electric circuit contact point 54 are respectively made of materials having conductivity such as a metal. The first electric circuit contact point 53 is electrically connected to the first control section of the image processing apparatus 13. More specifically, the first electric circuit contact point 53 configures a part of the first electric circuit. The first electric circuit contact point 53 of the receptacle section 32 abuts on the first electric circuit land 43 of the plug section 31, whereby the first electric circuit is formed.

The second electric circuit contact point 54 is electrically connected to the second control section of the image processing apparatus 13. More specifically, the second electric circuit contact point 54 configures a part of the second electric circuit. The second electric circuit contact point 54 of the receptacle section 32 abuts on the second electric circuit land 44 of the plug section 31, whereby the second electric circuit is formed.

Further, among a plurality of contact points which configure the first electric circuit contact points 53 and the second electric circuit contact point 54, a ground contact point 55 which is electrically connected to a ground potential, and a power supply contact point 56 which is connected to a power supply apparatus are provided to project in the extraction direction from the other contact points for transmitting signals. Further, the ground contact point 55 projects in the extraction direction from the power supply contact point 56.

The configuration as above is included, whereby when the plug section 31 is inserted into the receptacle section 32, the electric circuit in the endoscope 2 is electrically connected to the ground potential first, and thereafter, is supplied with power supply, and further thereafter, electrical connection for transmitting a signal with the control section 3 is performed. Electrical connection is performed in such a sequence, whereby protection and stability of the operation of the electric circuit in the endoscope 2 can be achieved.

In the inner surface portion of the first concave portion 51, a groove portion 57 in which the projection portion 45 provided at the first housing 41 of the plug section 31 is internally fitted is provided. As described above, the projection portion 45 and the groove portion 57 play the roles of a so-called key and key groove, and are for performing positioning around the center axis of the plug section 31 with respect to the receptacle section 32. The configuration in which the projection portion is provided at the receptacle section 32 and the groove portion is provided in the plug section 31 may be adopted.

In a bottom surface portion of the second concave portion 52 of the electric receptacle portion 50 which has the configuration as above, the light guide receptacle portion 60 and the conduit receptacle portion 61 are provided. The light guide receptacle portion 60 is a concave portion which can house the light guide plug 33, and the bottom surface portion side is connected to the light source section 21. The light guide plug 33 is housed in the light guide receptacle portion 60, whereby the light emitted from the light source section 21 is incident on the light guide fibers.

Further, the conduit receptacle portion 61 is a concave portion which can house the conduit plug 34, and the bottom surface portion side communicates with the air supply apparatus section 22 via a conduit not illustrated. The conduit plug 34 is housed in the conduit receptacle portion 61, whereby the air supply apparatus section 22 and the opening of the distal end portion 7 of the insertion portion 4 of the endoscope 2 communicates with each other.

On an outer periphery of the electric receptacle portion 50, a shell 62 in a substantially cylindrical shape made of a conductive material such as a metal is placed. Further, a cover 69 made of a material with electrical insulation properties such as a synthetic resin is provided in a periphery of the shell 62.

The shell 62 is electrically connected to a ground potential. The shell 62 covers the outer periphery of the electric receptacle portion 50, and projects in the extraction direction (opening direction of the first concave portion 51) from the electric receptacle portion 50.

A portion projected in the extraction direction from the electric receptacle portion 50, of the shell 62 is provided with a concave portion 63 having such an inside diameter that the flange portion 35 of the plug section 31 can be inserted in an interior thereof. When the plug section 31 is inserted into the receptacle section 32, the butt surface portion 36 of the flange portion 35 butts against a bottom surface portion 64 of the concave portion 63.

Further, at a side surface portion 65 of the concave portion 63 of the shell 62, a ball 67 which projects to inside in a radial direction of the concave portion 63 from the side surface portion 65 is placed. The ball 67 is configured by a material having conductivity such as a metal. The ball 67 is movable in the radial direction, and a moving range thereof is restricted so that the ball 67 does not project to inside in the radial direction by a predetermined amount or more from the side surface portion 65. In other words, the ball 67 is placed to be projectable/retractable to and from an inside of the concave portion 63 from the side surface portion 65 of the shell 62. A maximum projection amount of the ball 67 to the inside in the radial direction from the side surface portion 65 is within a range in which the ball 67 can abut on the first inclined surface portion 37 and the second inclined surface portion 38 of the flange portion 35 when the plug section 32 is inserted into the receptacle section 31.

More specifically, a holding hole portion 66 which is a through-hole in which the ball 67 can be inserted from outside in the radial direction is formed in a periphery of the concave portion 63 of the shell 62. The holding hole portion 66 is a tapered hole in which an inside diameter becomes smaller toward inside from outside in the radial direction of the shell 62. A shape of the holding hole portion 66 which is a tapered hole is set in accordance with a diameter of the ball 67, whereby the holding hole portion 66 holds the ball 67 in a state in which the ball 67 is projected by a predetermined amount to inside in the radial direction from the side surface portion 65, and can hold the ball 67 so that the ball 67 is movable in the radial direction. The holding hole portion 66 may be a countersunk hole.

At an outside of the holding hole portion 66, an urging member 68 which urges the ball 67 inserted in the holding hole portion 66 toward inside in the radial direction of the shell 62 is provided. The urging member 68 is configured by a material having conductivity such as a metal, and is fixed to the shell 62. In the present embodiment, the urging member 68 is a plate spring of a metal, and has a configuration which urges the ball 67 to a direction (inside in the radial direction) in which the ball 67 projects to an inside of the concave portion 63 from the side surface portion 65 of the shell 62 by an elastic force.

Figure 9:
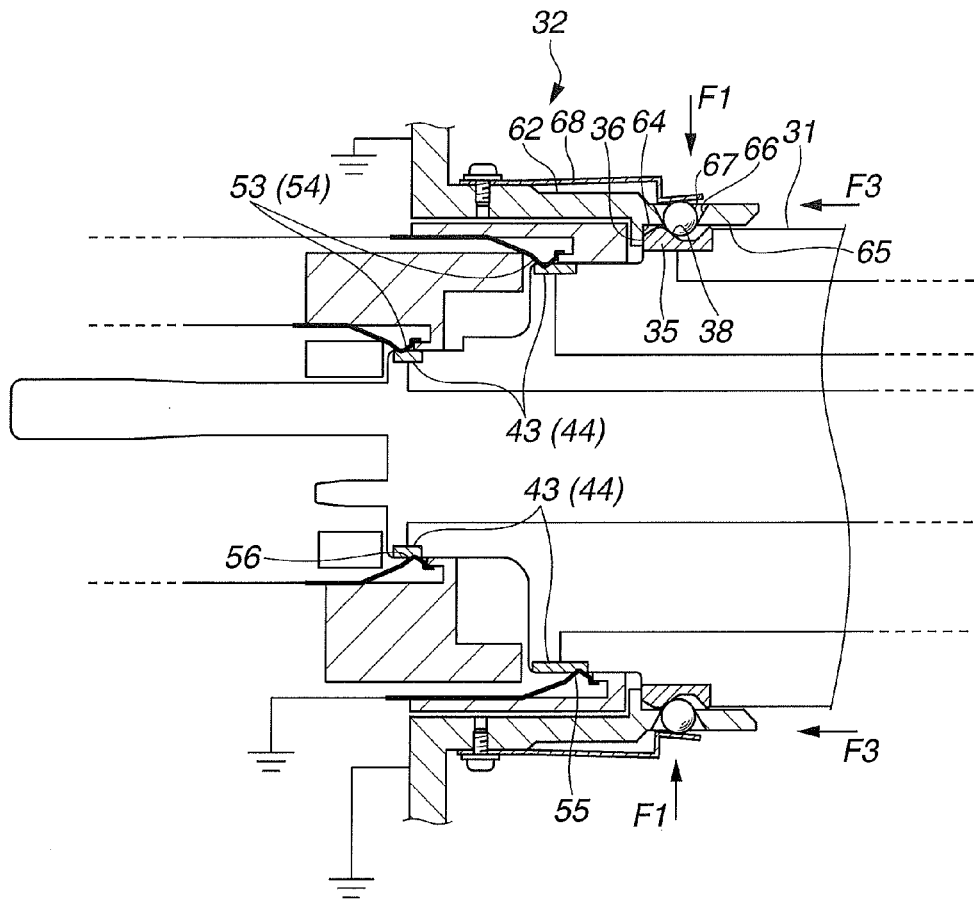
FIG. 9 is a view showing a state in which the plug section is inserted in the receptacle section.
Figure 10:
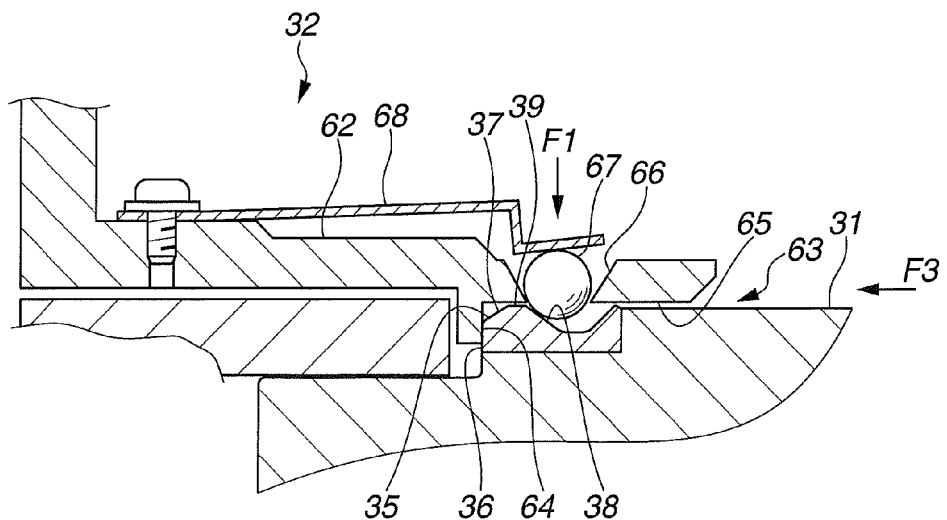
FIG. 10 is a view of an enlarged part of a ball and the flange portion of FIG. 9.

In the present embodiment, the ball 67 abuts on the second inclined surface portion 38 when the plug section 31 is inserted into the receptacle section 31 until the butt surface portion 36 butts against the bottom surface portion 64 of the concave portion 63 of the shell 62 as shown in FIG. 9 and FIG. 10. In this state, the ball 67 does not abut on the bottom surface of the holding hole portion 66, but is located halfway in the moving range.

Next, an operation in the case of a user of the endoscope apparatus 1 inserting the plug section 32 into the receptacle section 31 by using fingers in the connector system 30 described above will be described.

Figure 11:
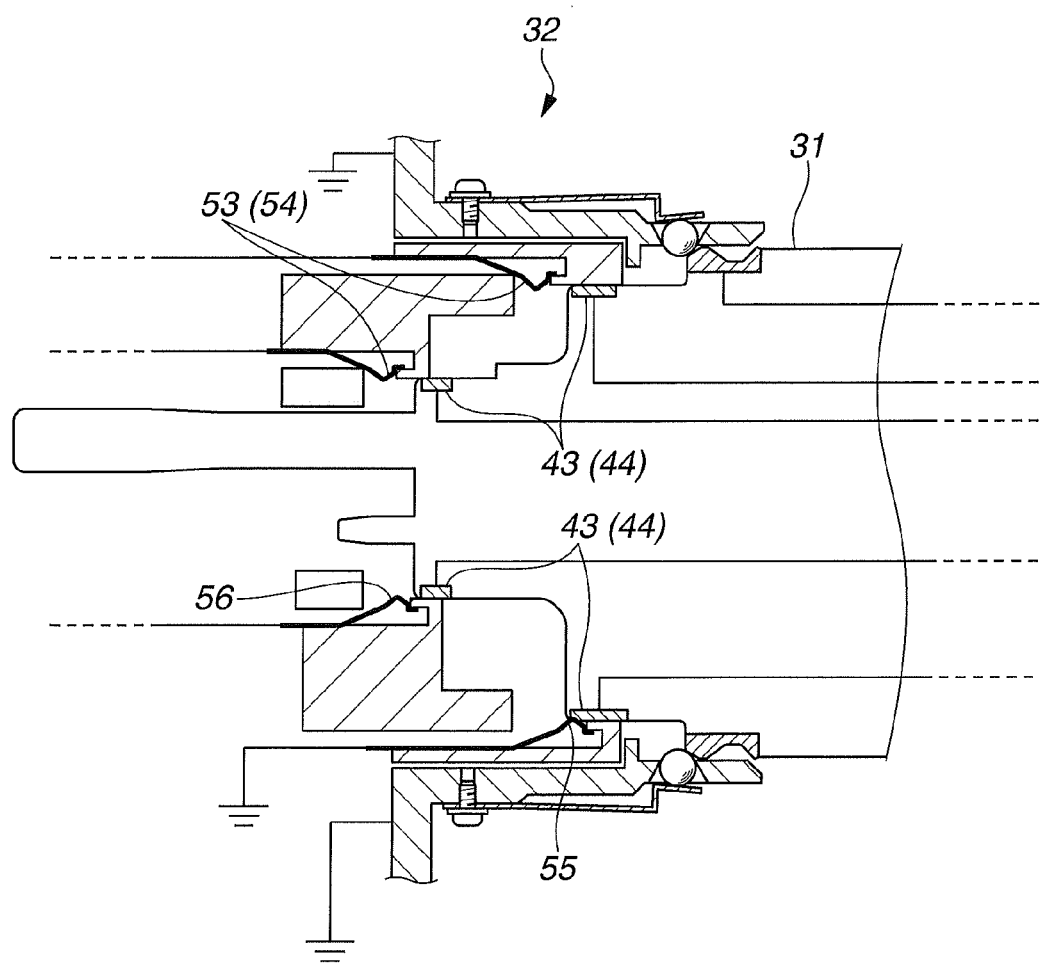
FIG. 11 is a view explaining an operation at the time of inserting the plug section into the receptacle section.

When the plug section 32 is inserted toward the insertion direction into the receptacle section 31 first, the ground contact point 55 and the corresponding lands of the first electric circuit lands 43 and the second electric circuit lands 44 abut on each other as shown in FIG. 11. Thereby, the electric circuit placed in the endoscope 2 is electrically connected to the ground potential.

Figure 12:
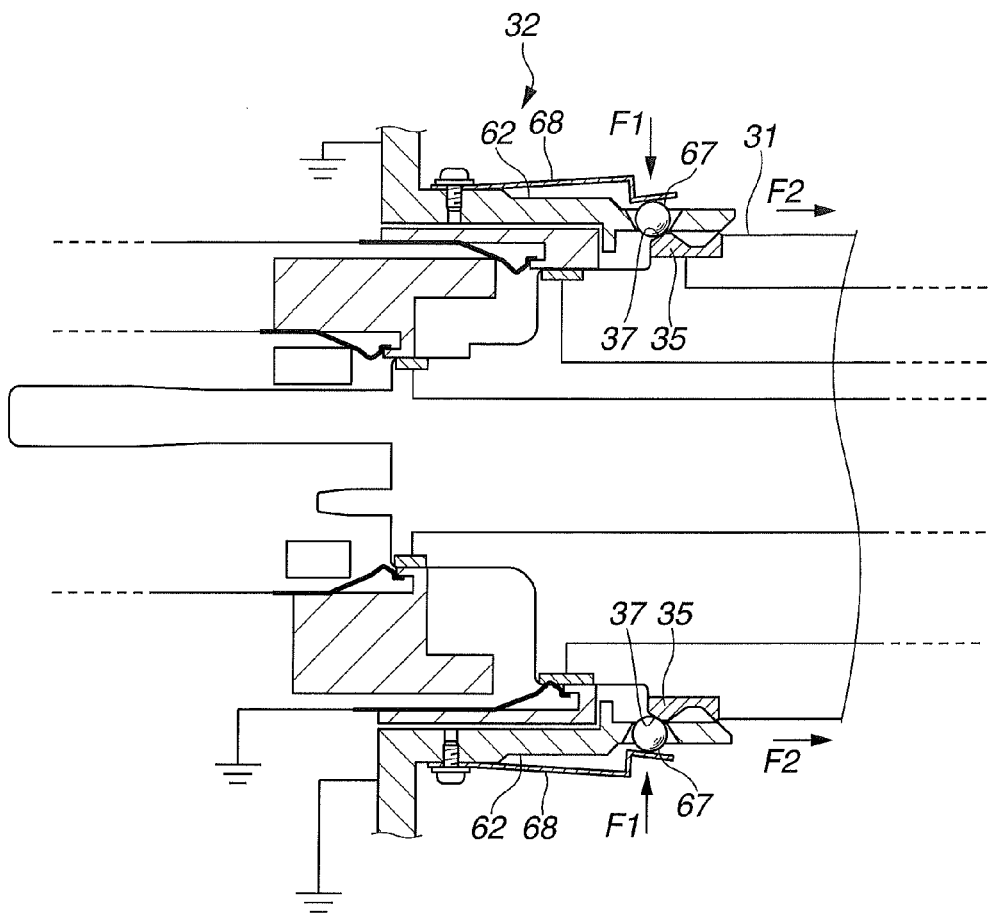
FIG. 12 is a view explaining the operation at the time of inserting the plug section into the receptacle section.
Figure 13:
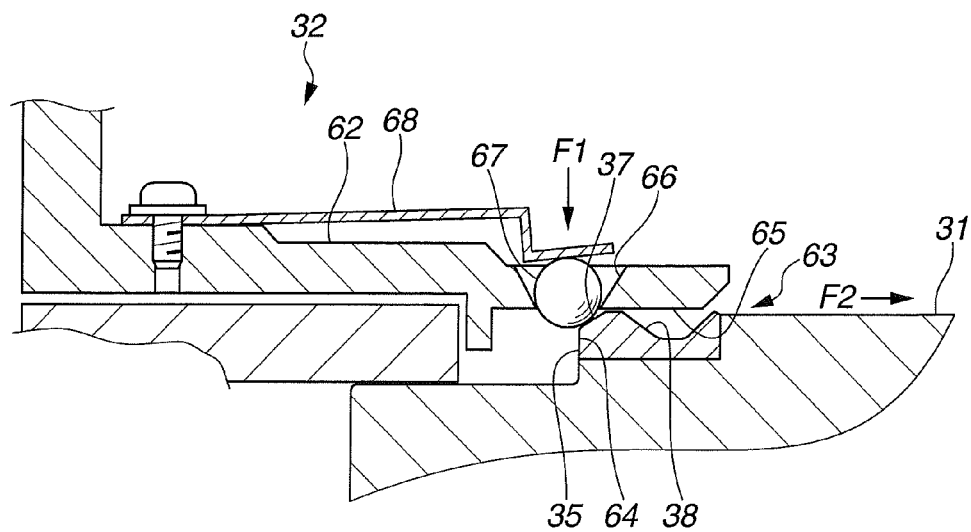
FIG. 13 is a view of an enlarged part of the ball and the flange portion of FIG. 12.

When the plug section 32 is further inserted toward the insertion direction, the ball 67 and the first inclined surface portion 37 of the flange portion 35 abut on each other, as shown in FIGS. 12 and 13. Here, the ball 67 is urged inside in the radial direction by the urging member 68 (arrow F1), and the first inclined surface portion 37 decreases in diameter toward the insertion direction. Accordingly, the urging force by the urging member 68 acts in the direction to push back the plug section 31 in the extraction direction to the plug section 31 (arrow F2).

When a hand is moved off from the plug section 31 in this state to eliminate the force that pushes the plug section 31 in the insertion direction, for example, the plug section 31 is pushed outside the receptacle section 32 by a reaction force.

Figure 14:
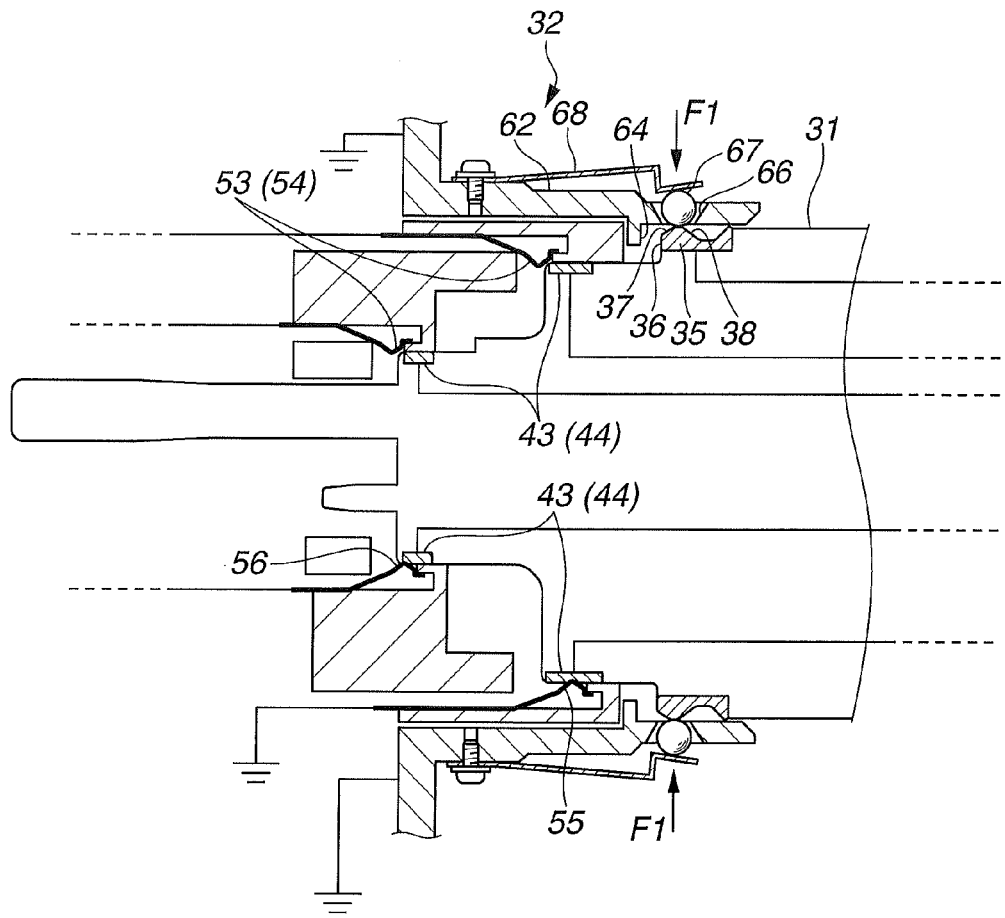
FIG. 14 is a view explaining an operation at the time of inserting the plug section into the receptacle section.

When the plug section 32 is further inserted toward the insertion direction with a stronger force than the reaction force by the urging force of the urging member 68, the power supply contact point 56 and the corresponding lands of the first electric circuit lands 43 and the second electric circuit lands 44 abut on each other, as shown in FIG. 14. Thereby, power supply to the electric circuit placed in the endoscope 2 is started.

Figure 15:
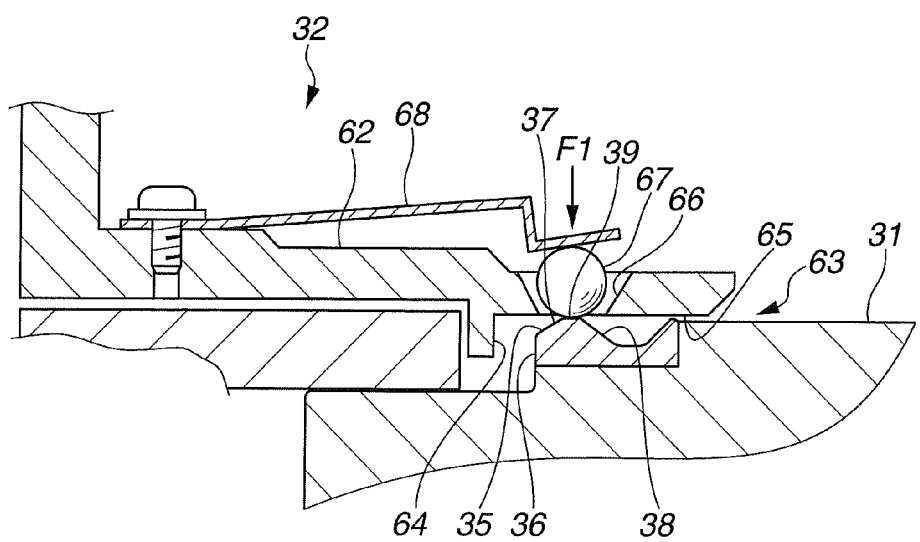
FIG. 15 is a view of an enlarged part of the ball and the flange section of FIG. 14.

Further, here, the ball 67 is pushed outside in the radial direction by the first inclined surface portion 37, and the ball 67 rides over the first inclined surface portion 37 to reach an outermost circumferential portion 39 of the flange portion 35, as shown in FIG. 15. Thereby, the reaction force which is generated by the urging force of the urging member 68 and pushes back the plug section 31 in the extraction direction is eliminated.

Figure 16:
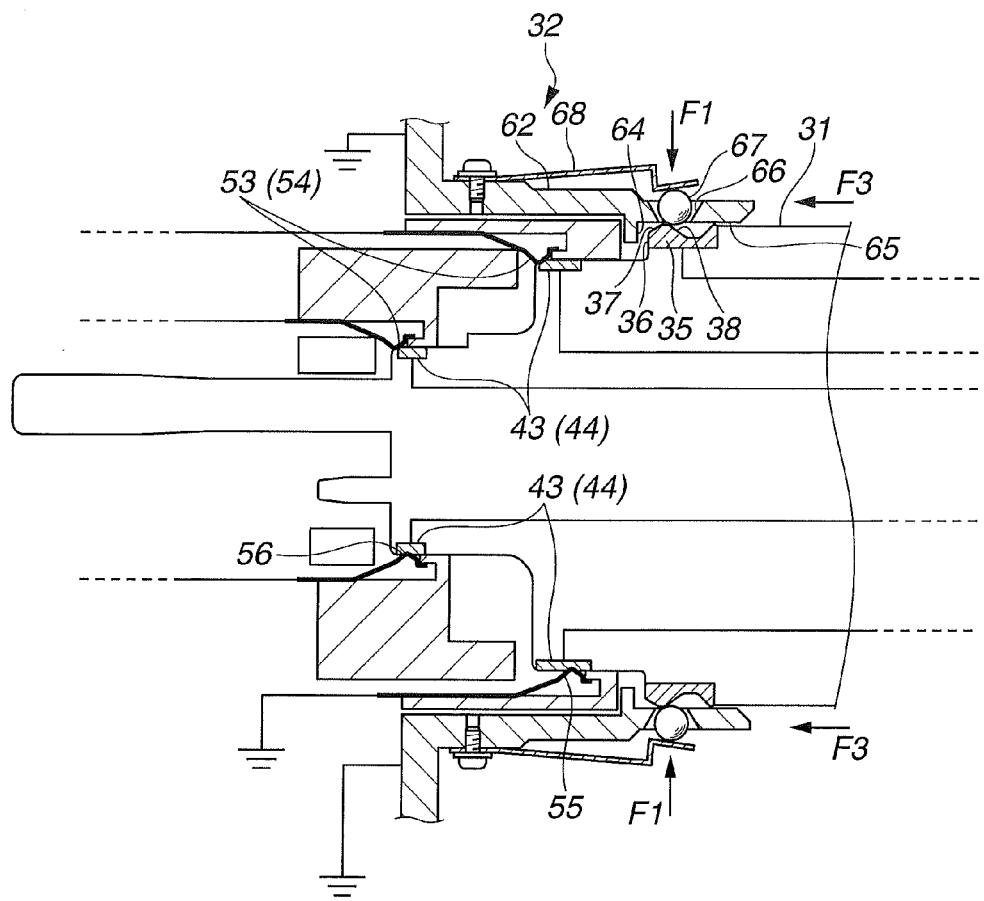
FIG. 16 is a view explaining an operation at the time of inserting the plug section into the receptacle section.
Figure 17:
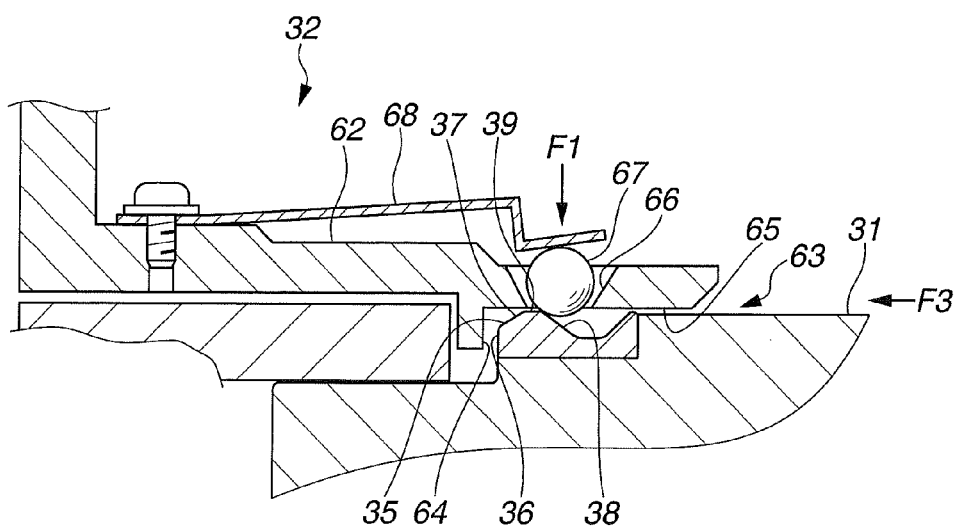
FIG. 17 is a view of an enlarged part of the ball and the flange section of FIG. 16.

In this instant, the user pushes the plug section 31 in the insertion direction with a force larger than the reaction force. Therefore, the plug section 31 further moves in the insertion direction, and the ball 67 rides over the outermost circumferential portion 39 of the flange portion 35, and thereafter, falls toward the bottom surface direction of the holding hole portion 66 along the second inclined surface portion 38, as shown in FIG. 16 and FIG. 17.

Here, the second inclined surface portion 38 decreases in diameter toward the extraction direction. Accordingly, the urging force (arrow F1) by the urging member 68 acts onto the plug section 31 as a propulsive force which propels the plug section 31 in the insertion direction (arrow F3). Even if the user takes the hand off the plug section 31 in this state, the plug section 31 is automatically drawn into the receptacle section 32.

Further, in the position where the ball 67 rides over the first inclined surface portion 37 and abuts on the second inclined surface portion 38, the first electric circuit lands 43 and the second electric circuit lands 44 for transmitting a signal such as a video signal which do not abut on the first electric circuit contact points 53 and the second electric circuit contact points 54 yet abut on the first electric circuit contact points 53 and the second electric circuit contact points 54.

In general, in order to cause the contact points and the lands to abut on one another in the connector with multiple pins, the plug section needs to be pushed in with the power corresponding to the number of contact points, but in the present embodiment, the plug section 31 is automatically drawn into the receptacle section 32 so that the contact points and the lands abut on each other by the propulsive force (arrow F3) which is generated by the urging force of the urging member 68.

As shown in FIG. 9 and FIG. 10, the plug section 31 is inserted into the receptacle section 32 until the butt surface portion 36 butts against the bottom surface portion 64 of the concave portion 63 of the shell 62. In this state, the ball 67 does not abut on the bottom surface of the holding hole portion 66, and is located halfway in the moving range, and therefore, the propulsive force (arrow F3) which is generated by the urging force of the urging member 68, and pushes the plug section 31 in the insertion direction remains to be generated.

When the plug section 31 is extracted from the above state, a power larger than the power which is required when the plug section 31 is inserted needs to be applied in the extraction direction, because the inclination angle β of the second inclined surface portion 38 is larger than the inclination angle α of the first inclined surface portion 37.

Therefore, in the present embodiment, in the state in which the plug section 31 is inserted in the receptacle section 32, a play between the receptacle section 32 and the plug section 31 is eliminated to perform electric connection reliably, and the plug section 31 can be prevented from unintentionally falling off from the receptacle section 32.

The connector system 30 of the present embodiment as above includes, in the plug section 31, the flange portion 35 including the first inclined surface portion 37 which increases in diameter toward the extraction direction, and the second inclined surface portion 38 which decreases in diameter toward the extraction direction on the extraction direction side of the first inclined surface portion 37, and includes, in the receptacle section 32, the ball 67 which is urged to inside in the radial direction by the urging member 68, and abuts on the flange portion 35.

In the connector system 30 having the configuration as above, the plug section 31 falls off from the receptacle section 32 by the reaction force which is generated by the action of the ball 67 and the first inclined surface portion 37, unless the plug section 31 is inserted to the position where the ball 67 urged to inside in the radial direction rides over the first inclined surface portion 37, as shown in FIG. 15.

Meanwhile, as shown in FIG. 17, if the plug section 31 is inserted to the position where the ball 67 urged to inside in the radial direction rides over the first inclined surface portion 37 and the outermost circumferential portion 39, the plug section 31 is reliably inserted into the receptacle section 32 until the butt surface portion 36 butts against the receptacle section 32 by the propulsive force which is generated by the action of the ball 67 and the second inclined surface portion 38 even if the hand is taken off the plug section 31. Even after the plug section 31 is inserted into the receptacle section 32, the plug section 31 is pushed in the insertion direction by the propulsive force, and therefore, the plug section 31 does not fall off from the receptacle section 32 unintentionally due to vibration or the like.

As above, in the connector system 30 of the present embodiment, the result of the case in which the user inserts the plug section 31 into the receptacle section 32 is any one of two states that are the state in which the plug section 31 is reliably inserted in the receptacle section 32, or the state in which the plug section 31 falls off from the receptacle section 32.

More specifically, the user can clearly recognize whether or not the electrical connection is reliably performed in the connector system 30. Consequently, according to the connector system 30 of the present embodiment, electrical connection can be reliably performed while the plug section 31 is detachable only by a simple operation of inserting/extracting the plug section 31 to/from the receptacle section 32.

Further, in the connector system 30 of the present embodiment, the electromagnetic shield member placed in the endoscope 2 is electrically connected to the flange portion 35 having conductivity. Meanwhile, in the state in which the plug section 31 is inserted in the receptacle section 32, the ball 67 which abuts on the flange portion 35 and has conductivity is connected to the ground potential via the urging member 68 and the shell 62 which similarly have conductivity. Accordingly, in the present embodiment, the electromagnetic shield member can be electrically connected to the ground potential reliably, and electromagnetic noise which is irradiated from the endoscope 2 can be suppressed.

Figure 18:
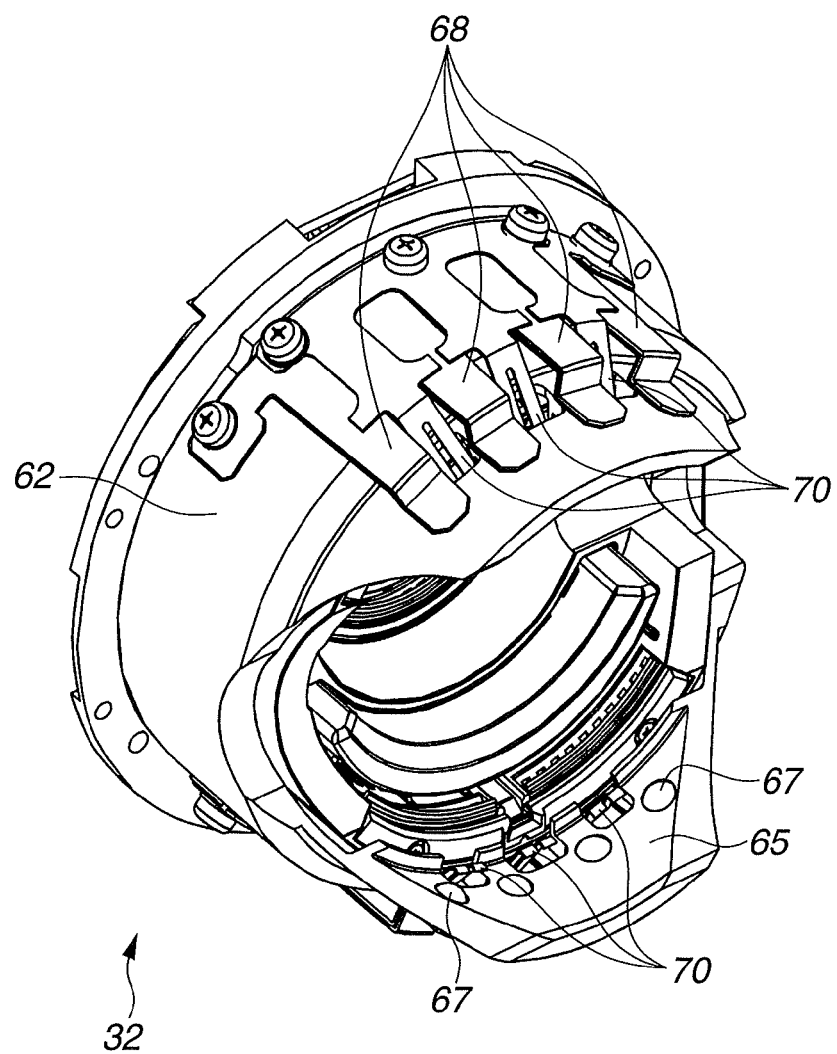
FIG. 18 is a view showing a modified example of the receptacle section.

As shown in FIG. 18, a plurality of tongue piece portions 70 which are extended to inside in the radial direction from the side surface portion 65 of the concave portion 63 and is made of a conductive material such as a metal are provided at the shell 62, and the tongue piece portions 70 may be configured to abut on the flange portion 35 in the state in which the plug section 31 is inserted in the receptacle section 32. According to the configuration like this, the tongue piece portion 70 contacts the flange portion with a larger area than the ball 67, and therefore, the flange portion 35 can be electrically connected to the ground potential more reliably.

The present invention is not limited to the aforementioned embodiment, and can be properly changed within the range without departing from the gist or the idea of the invention that can be read from claims and the entire description, and the connector systems accompanied by such changes are also included in the technical range of the present invention.

What is claimed is:

1. A connector system, comprising
a plug section provided at a universal cord section of an endoscope,
a land provided at the plug section and having conductivity,
a receptacle section provided at a control section to which the endoscope is connected to receive a signal from the endoscope via the land, and having a concave portion in an inside of which the plug section can be inserted,
a ground contact point which is electrically connected to a ground potential and provided at the receptacle section, the ground contact point having conductivity, and
an electrical contact point which is different from the ground contact point and provided at the receptacle section, the electric contact point having conductivity,
in which the plug section is inserted into or extracted from the receptacle section, whereby the land, and the ground contact point and the electric contact point are caused to abut on each other or separate from each other,
wherein the plug section includes a flange portion including a first inclined surface portion which increases in diameter toward an extraction direction, and a second inclined surface portion which decreases in diameter toward the extraction direction on an extraction direction side of the first inclined surface portion, in which an inclination angle with respect to an insertion direction of the second inclined surface portion is larger than an inclination angle with respect to the insertion direction of the first inclined surface portion,
the receptacle section includes a ball which is placed to be projectable/retractable from a side surface portion of the concave portion, and to be capable of abutting on the first inclined surface portion and the second inclined surface portion of the flange portion when the plug section is inserted, and an urging member which urges the ball in a direction to project into the concave portion from the side surface portion,
the ground contact point abuts on and electrically connects with the land at a position where the ball of the receptacle section abuts on the first inclined surface portion, when the plug section is inserted into the receptacle section, and
the plug section is further inserted into the receptacle section and thereby the electric contact point abuts on and electrically connects with the land at a position where the ball and the second inclined surface portion abut on each other, while the ground contact point continues to abut on the land.

* * * * *